(12) United States Patent
Kudo et al.

(10) Patent No.: US 6,802,932 B2
(45) Date of Patent: Oct. 12, 2004

(54) ABSORBENT ARTICLE AND METHOD OF MANUFACTURING THE SAME

(75) Inventors: Jun Kudo, Kagawa (JP); Mitsuhiro Wada, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 161 days.

(21) Appl. No.: 10/162,940

(22) Filed: Jun. 4, 2002

(65) Prior Publication Data

US 2002/0193765 A1 Dec. 19, 2002

(30) Foreign Application Priority Data

Jun. 8, 2001 (JP) ........................................ 2001-174774
Mar. 20, 2002 (JP) ........................................ 2002-077746

(51) Int. Cl.$^7$ .............................................. B32B 31/00
(52) U.S. Cl. ...................... 156/322; 156/62.4; 156/207; 156/205; 156/209; 156/219; 156/292; 604/370; 604/372

(58) Field of Search ................................. 604/370, 372; 156/62.4, 187, 191, 192, 207, 206, 205, 209, 219, 220, 290, 292, 322

(56) References Cited

U.S. PATENT DOCUMENTS 4,629,457 A * 12/1986 Ness .......................... 604/382

* cited by examiner

*Primary Examiner*—Linda L Gray
(74) *Attorney, Agent, or Firm*—Darby & Darby (57) ABSTRACT

A method for manufacturing an absorbent article including: a topsheet formed from a nonwoven fabric; a backsheet; and a cushion layer disposed between the topsheet and the backsheet is achieved by applying heat to a cushion layer unwound from a material roll to restore the bulkiness of the tissue layer, blowing air into the cushion layer for rapid cooling after the application of heat to maintain the restored bulkiness of the cushion layer, and laminating the topsheet, cushion layer, and the backsheet onto each other.

7 Claims, 5 Drawing Sheets

ABSORBENT ARTICLE AND METHOD OF MANUFACTURING THE SAME

BACKGROUND OF THE INVENTION

1. Field of the Invention

The present invention relates to a thin absorbent article such as a vaginal discharge absorbing sheet called panty liner or a urine absorbing sheet for an incontinence patient, more specifically, to the absorbent article which provides an excellent cushiony feeling even though it is sufficiently thin, and a method of manufacturing the same.

2. Description of the Related Art

As a thin absorbent article, a vaginal discharge absorbing sheet called panty liner has been widely known. Such absorbing sheet is worn by fixing it on the inner side of a crotch portion of an undergarment through a pressure sensitive adhesive. Generally, this conventional absorbing sheet has a thin absorbent layer between a liquid-impermeable backsheet and a topsheet formed from a spunlaced nonwoven fabric or the like. The absorbent layer is generally formed from a plurality of sheets of tissue paper stacked one on another, air laid pulp, or the like.

The absorbing sheet is preferred to provide the wearer with a soft feeling equivalent to that of the undergarment. Especially, since the topsheet comes into contact with the wearer's skin, specifically the female genital organ, its contact feeling should be soft. However, in the case where the topsheet is formed from a flat nonwoven fabric such as spunlaced nonwoven fabric, it can not provide a good contact feeling. In addition, the topsheet can not provide a soft appearance when viewed by the wearer upon wearing.

In case of a relatively thick absorbent article such as a sanitary napkin, on the other hand, a good cushiony feeling can be provided to the wearer's skin by shaping its topsheet to have ridge portions and groove portions significantly different in level. However, since the basic structure of the vaginal discharge absorbing sheet, which should be felt as a part of the undergarment in use while being fixed on the inner side of the crotch portion of the undergarment, must be significantly thin, it is substantially impossible to shape the topsheet to have ridge portions and groove portions significantly different in level.

In order to provide the wearer with a soft wearing feel equivalent to that of the undergarment as well as a soft appearance, nevertheless, it is still possible to shape the topsheet to have ridge portions and groove portions slightly different in level. However, since the absorbent layer underlying the topsheet having such ridge and groove portions is thin and relatively hard, the difference in level between the ridge and groove portions of the topsheet is removed or reduced in the manufacturing process of the thin absorbent article. Therefore, the originally expected soft feeling can not be obtained.

In addition, since the absorbent article of this kind is generally folded and wrapped so as to improve the portability by the user, the difference in level between the ridge and groove portions is also removed or reduced easily by the pressure applied in the folding and wrapping process or the pressure applied when it is stored in such wrapped state.

SUMMARY OF THE INVENTION

The present invention has been worked out in view of the shortcoming in the prior art set forth above. It is therefore an object of the present invention to provide a thin absorbent article which is capable of providing a soft contact feeling to the wearer's skin as well as a soft appearance, and is also capable of maintaining such soft feeling.

It is another object of the present invention to provide a method of manufacturing an absorbent article which is capable of maintaining a soft feeling constantly.

According to a first aspect of the invention, there is provided an absorbent article comprising: a topsheet formed from a nonwoven fabric; a backsheet; and a cushion layer disposed between the topsheet and the backsheet, wherein the topsheet is three-dimensionally shaped to have hills and valleys alternating with each other, the hills and the valleys being arranged at a pitch of 0.5 to 5 mm, the three-dimensionally shaped topsheet having a thickness of 0.5 to 5 mm under a condition where a pressure of 49 Pa is applied thereto, the cushion layer, under a condition where a pressure of 49 Pa is applied thereto, has a thickness equal to or larger than the thickness of the topsheet, and the cushion layer has a compression property value smaller than that of the topsheet.

With such construction, the difference in level between the hills and the valleys of the topsheet is hardly removed or reduced even if an external pressure is applied thereto in the manufacturing process or after wrapping. Therefore, the absorbent article can constantly provide a soft contact feeling to the skin as well as a soft appearance.

Preferably, the thickness of the cushion layer under a condition where a pressure of 49 Pa is applied thereto is one to five times the thickness of the topsheet. Within such range, the absorbent article can be made thin as a whole.

For example, the cushion layer is formed from a through-air bonded nonwoven fabric comprising thermoplastic fibers. The through-air bonded nonwoven fabric has an excellent cushioning property even if it is of the thin type, thereby effectively preventing the three-dimensionally shaped topsheet from being crushed.

It is possible that the topsheet mainly absorbs and retains a liquid and the cushion layer substantially does not have a function of retaining a liquid. Alternatively, it is also possible that the cushion layer substantially has a function of absorbing and retaining a liquid. In this case, the main body of the absorbent article may be composed of only three layers, i.e., the topsheet, the cushion layer and the backsheet. Therefore, the main body can be made thin and felt as integrated with an undergarment when fixed on the inner side of the undergarment in use.

In an alternative to the three-layer structure, it is also possible to construct the main body to have at least four layers by providing an absorbent layer having a function of absorbing and retaining a liquid between the cushion layer and the backsheet. With the absorbent layer being thus provided, the absorbent article can absorb and retain more liquid as compared with the case where the main body is composed of only three layers.

In this case, the absorbent layer may be formed from an air-laid nonwoven fabric comprising pulp. By employing the air-laid nonwoven fabric comprising pulp as the absorbent layer, the absorbent layer can absorb and retain more liquid than the cushion layer even if it is of the thin type.

Accordingly, the absorbent article of the present invention is preferably used as a vaginal discharge absorbing sheet. However, the absorbent article of the present invention is also applicable to a thin urine absorbing sheet for incontinence patients.

According to another aspect of the present invention, there is provided a method for manufacturing an absorbent article including: a topsheet formed from a nonwoven fabric; a backsheet; and a cushion layer disposed between the topsheet and the backsheet, the method comprising applying heat to the cushion layer unwound from a material roll to restore bulkiness of the cushion layer, before laminating the topsheet, the cushion layer and the backsheet.

In the manufacturing method, even if the cushion layer is in a compressed state when supplied from the material roll, it is heated to restore the bulkiness, thereby providing a soft feeling to the manufactured absorbent article.

Preferably, the absorbent article manufacturing method further comprises cooling the cushion layer after applying heat to the cushion layer. With the cooling process, the restored bulkiness can be set immediately.

Preferably, the cushion layer is formed from a through-air bonded nonwoven fabric comprising thermoplastic fibers. Even if it is once compressed to reduce thickness, the through-air bonded nonwoven fabric comprising thermoplastic fibers can easily restore its bulkiness when heat is applied thereto.

It is also possible that the absorbent article manufacturing method further comprises disposing an absorbent layer, which has a function of absorbing and retaining a liquid, between the cushion layer and the backsheet. In this case, it is preferred that the absorbent article manufacturing method further comprises applying heat to the absorbent layer unwound from a material roll to restore bulkiness of the absorbent layer, before disposing the absorbent layer between the cushion layer and the backsheet. With the bulkiness of the absorbent layer being restored, the absorbent layer can absorb and retain more liquid. It is also preferred that the absorbent article manufacturing method further comprises cooling the absorbent layer after applying heat to the absorbent layer. With the cooling process, the restored bulkiness of the absorbent layer can also be set immediately.

For example, the absorbent layer is formed from an air-laid nonwoven fabric comprising pulp. The bulkiness of the air-laid nonwoven fabric can also be restored by applying heat thereto.

It is also preferred that the topsheet is three-dimensionally shaped to have hills and valleys alternating with each other, the hills and the valleys are arranged at a pitch of 0.5 to 5 mm, and the three-dimensionally shaped topsheet having a thickness of 0.5 to 5 mm under a condition where a pressure of 49 Pa is applied thereto. Since the bulkiness of the cushion layer is restored in the manufacturing method, the difference in level between the hills and the valleys of the topsheet can be easily prevented.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
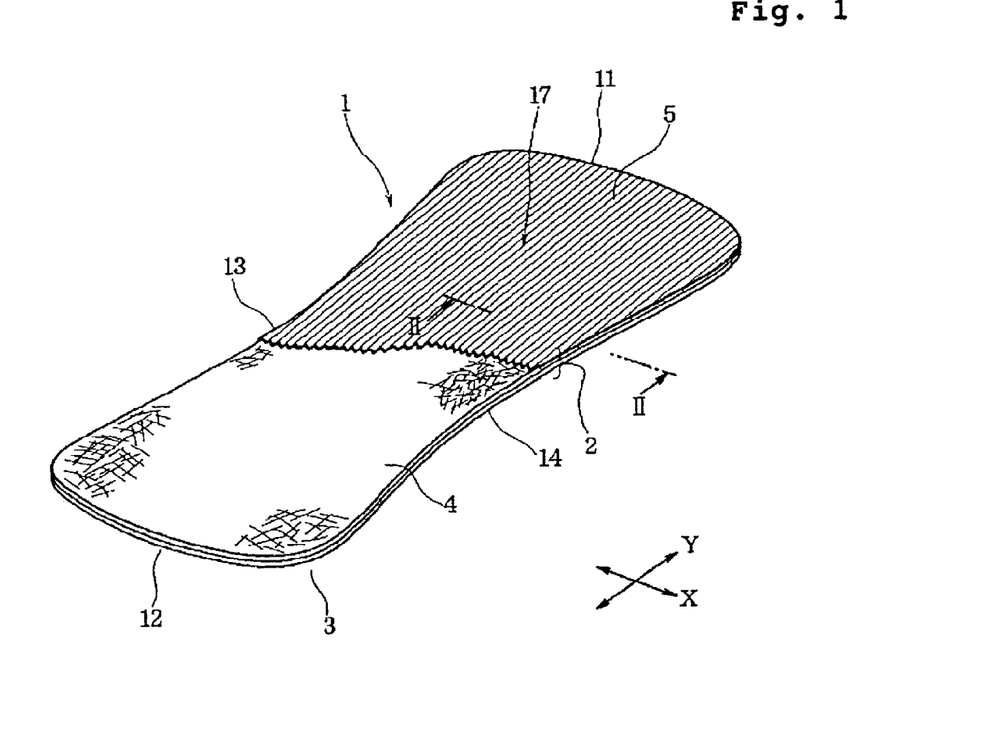
FIG. 1 is a partly cut-away perspective view shows a vaginal discharge absorbing sheet as an absorbent article according to a first embodiment of the present invention.
Figure 2:
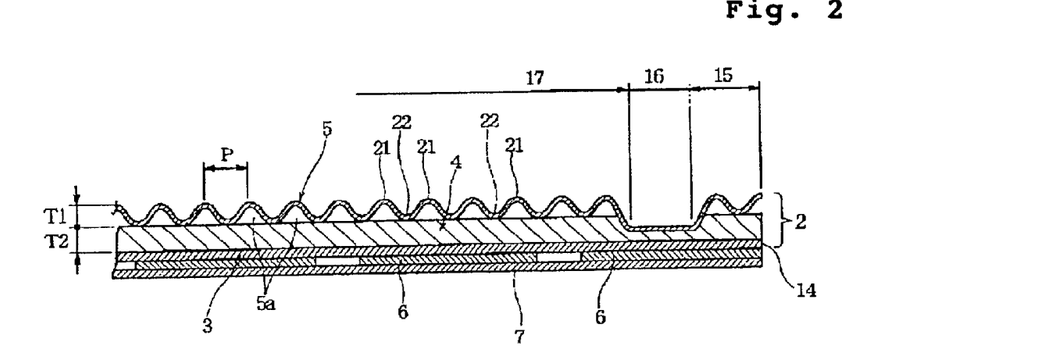
FIG. 2 is a sectional view of a portion of the vaginal discharge absorbing sheet taken along line II—II of FIG. 1.

FIG. 1 is a partly cut-away perspective view shows a vaginal discharge absorbing sheet (called panty liner) 1 as a thin absorbent article according to a first embodiment of the present invention. FIG. 2 is a sectional view of a portion of the vaginal discharge absorbing sheet 1 taken along line II—II of FIG. 1.

As used herein, the term "vaginal discharge absorbing sheet" refers to a thin absorbent article to be worn by female while being integrated with an undergarment by fixing it on the inner side of a crotch portion of the undergarment. The vaginal discharge absorbing sheet is aimed at absorbing a vaginal discharge from the female genital organ. However, it should be noted that the thin absorbent article of the present invention is also applicable to an absorbent article which is to be worn by female by fixing it on the inner side of the crotch portion of the undergarment for absorbing a minute amount of urine upon incontinence.

The absorbing sheet 1 has a main body 2, which is a three-layer laminate comprising: a backsheet 3; a cushion layer 4 disposed on the backsheet 3; and a topsheet 5 disposed on the cushion layer 4.

On the rear surface of the main body 2 (i.e., on the exterior surface of the back sheet 3), as shown in FIG. 2, there is provided a pressure sensitive adhesive layer 6 for fixation to the undergarment. This pressure sensitive adhesive layer 6 is applied in parallel stripes, which extend linearly in a longitudinal direction (Y-direction) of the main body 2 and are spaced apart from each other in a width direction (X-direction) of the main body 2. The exterior surface of the pressure sensitive adhesive layer 6 is covered with a release sheet 7.

All the backsheet 3, cushion layer 4, topsheet 5 and release sheet 7 are of the same shape and size. As will be described later with reference to a manufacturing method, the backsheet 3, cushion layer 4, topsheet 5 and release sheet 7 are stacked and then trimmed all together into the shape shown in FIG. 1.

As shown in FIG. 1, the absorbing sheet 1 is of substantially hourglass shape, wherein: end edges 11 and 12 to be directed to the wearer's abdomen and buttocks are curved to protrude outwardly; two longitudinally-extending side edges 13 and 14 are curved to dent inwardly.

FIG. 2 shows a predetermined width of seal portion 16, which is formed along but spaced away from the side edge 14 by a predetermined with of peripheral portion 15. Similarly, the peripheral portion 15 and the seal portion 16 are formed along the end edges 11, 12 and the other side edge 13 to extend continuously along the whole periphery of the main body 2. The region inside of the seal portion 16 thus extending continuously along the whole periphery is called a main liquid-receiving region 17.

The backsheet 3 is liquid-impermeable. For example, the backsheet 3 may be formed from a thin polyethylene film having a basis weight of 10 to 30 g/m$^2$. The polyethylene film is preferably provided with fine apertures to have moisture permeability (breathability). In an alternative, the backsheet 3 may be formed from a hydrophobic nonwoven fabric.

Here, the relationship between the topsheet 5 and the cushion layer 4 may be such that:

(1) The topsheet 5 is hydrophilic and liquid-permeable, and the cushion layer 4 is hydrophilic and has the function of absorbing and retaining a liquid; or (2) The topsheet 5 is hydrophilic and mainly has the function of absorbing a liquid, and the cushion layer 4 substantially does not function to retain a liquid.

In case of (2), when a liquid is absorbed by the topsheet 5, a part of the liquid may possibly migrate to the cushion layer 4. However, the cushion layer 4, which substantially does not function to retain a liquid, is allowed to absorb only a smaller amount of liquid per unit volume than the topsheet 5.

The topsheet 5 is formed from a hydrophilic nonwoven fabric. In case of (1), the topsheet 5 may be composed mainly of synthetic fibers treated to be hydrophilic. If desired, the topsheet 5 may contain hydrophilic fibers such as cotton or rayon. In case of (2), the topsheet 5 may be formed by mixing absorbent, hydrophilic fibers such as cotton or rayon with synthetic fibers treated to be hydrophilic, or only of the hydrophilic fibers such as cotton or rayon.

In the shown embodiment, the nonwoven fabric forming the topsheet 5 is a wet-laid spunlaced nonwoven fabric, which is formed by applying water jets to a wet fiber web formed on a net wire to entangle fibers about each other. Since the wet-laid spunlaced nonwoven fabric has a soft surface and provides a soft feeling to the touch, it is desirable as the nonwoven fabric forming the topsheet 5.

For the topsheet 5, the wet-laid spunlaced nonwoven fabric thus formed is then three-dimensionally shaped (e.g., corrugated) to have ridge portions (hills) 21 and groove portions (valleys) 22 alternating with each other in the width direction (X-direction). The ridge portions 21 and the groove portions 22 extend parallel with one another in the longitudinal direction (Y-direction). As will be described later, the ridge portions 21 and the groove portions 22 can be formed by heating the wet-laid spunlaced nonwoven fabric under pressure between forming rolls. It should be noted that the topsheet of the present invention is not limited to such a corrugated configuration as long as having hills and valleys alternating with each other. For example, the topsheet may have embossed dot patterns or diamond patterns.

The basis weight of the wet-laid spunlaced nonwoven fabric preferably ranges between 15 and 50 g/m$^2$. The ridge portions 21 and the groove portions 22 form relatively fine undulations, and the pitch P of the ridge portions 21 and the groove portions 22 is from 0.5 to 5 mm, more preferably from 1 to 3 mm. When a pressure of 49 Pa is applied to the three-dimensionally shaped topsheet 5 with a circular pressure plate of 2 cm$^2$ by using Automatic Compression Tester "KES FB-3A" manufactured by Kato Tech, Japan, the thickness T1 is in a range of 0.5 to 5 mm. More preferably, the thickness T1 is from 0.5 to 3 mm.

The nonwoven fabric forming the topsheet 5 is not limited to the wet-laid spunlaced nonwoven fabric, as long as the basis weight, the pitch P and the thickness T1 can be set within the foregoing ranges. For example, use can be made of a dry-laid spunlaced nonwoven fabric formed by applying water jets to a dry-laid fiber web to entangle fibers about each other, a spunbonded nonwoven fabric comprising continuous thermoplastic filaments, a through-air bonded nonwoven fabric in which thermoplastic fibers are partly fusion-bonded with heated air, and so on.

The wet-laid spunlaced nonwoven fabric and the dry-laid spunlaced nonwoven fabric are applicable to both the cases (1) and (2), and may contain 0 to 90% by weight of moisture-absorbent, hydrophilic fibers such as rayon and/or cotton and 10 to 100% by weight of thermoplastic synthetic fibers. On the other hand, the spunbonded nonwoven fabric and the through-air bonded nonwoven fabric are formed only of thermoplastic synthetic fibers treated to be hydrophilic, and mainly used for the case (1).

The synthetic fibers may be monocomponent fibers of polyethylene (PE), polypropylene (PP) or polyethylene terephthalate (PET), or bicomponent fibers of combinations thereof. Alternatively, nylon (Ny) may be selected for the synthetic fibers.

The cushion layer 4 has the function of cushioning the topsheet 5, and is preferably formed from a through-air bonded nonwoven fabric comprising thermoplastic synthetic fibers.

The through-air bonded nonwoven fabric wound in the form of material roll, is unwound from the material roll and heated with a heat roll or by applying heated air to increase the bulkiness (thickness) by 1.5 to 8 times to approach the original bulkiness (bulkiness before winding), followed by rapid cooling. The through-air bonded nonwoven fabric thus heated and rapidly cooled is used as the cushion layer 4.

In the case where the cushion layer 4 is formed from a through-air bonded nonwoven fabric comprising thermoplastic fibers, as set forth above, the nonwoven fabric is preferably heated in the foregoing heating process up to a temperature equal to or higher than the lowest one of the softening temperatures of the materials forming the nonwoven fabric. In this case, it is more preferred that the nonwoven fabric is heated up to a temperature equal to or higher than the highest one of the softening temperatures of the materials forming the nonwoven fabric. For example, in case where the nonwoven fabric comprises PE fibers, the PE fibers will be softened at a temperature of about 115° C.

Thereafter, the heated nonwoven fabric is rapidly cooled down to a temperature below the softening temperature, thereby preventing the heated nonwoven fabric from undesirably extending and decreasing in bulkiness.

The through-air bonded nonwoven fabric is preferred to have a basis weight in a range between 15 and 60 g/m$^2$, and a fiber density in a range between 0.013 and 0.015 g/cm$^3$ after the restoration of bulkiness.

The thickness T2, which is determined when a pressure of 49 Pa is applied to the cushion layer 4 along by using the foregoing Automatic Compression Tester, is equal to or larger than the thickness T1 of the topsheet 5. The thickness T2 of the cushion layer 4 is preferably 1 to 5 times the thickness T1 of the topsheet 5, more preferably 2 to 5 times.

Throughout the disclosure, the thickness T1 of the topsheet 5, the thickness T2 of the cushion layer 4, and compression properties of the respective topsheet 5 and cushion layer 4 are expressed by values determined by using the foregoing Automatic Compression Tester "KES FB-3A" manufactured by Kato Tech.

For measurement of such values, the topsheet 5 (or the cushion layer 4) alone is put on the Automatic Compression Tester. Then, an initial pressure P0=49 Pa (0.5 g/cm²) is applied to the topsheet 5 (or the cushion layer 4) with the circular pressure plate having an area of 2 cm². The respective thicknesses thus measured for the topsheet 5 and the cushion layer 4 are designated by T1 and T2. In addition, the LC value is measured and called compression property value.

Figure 5:
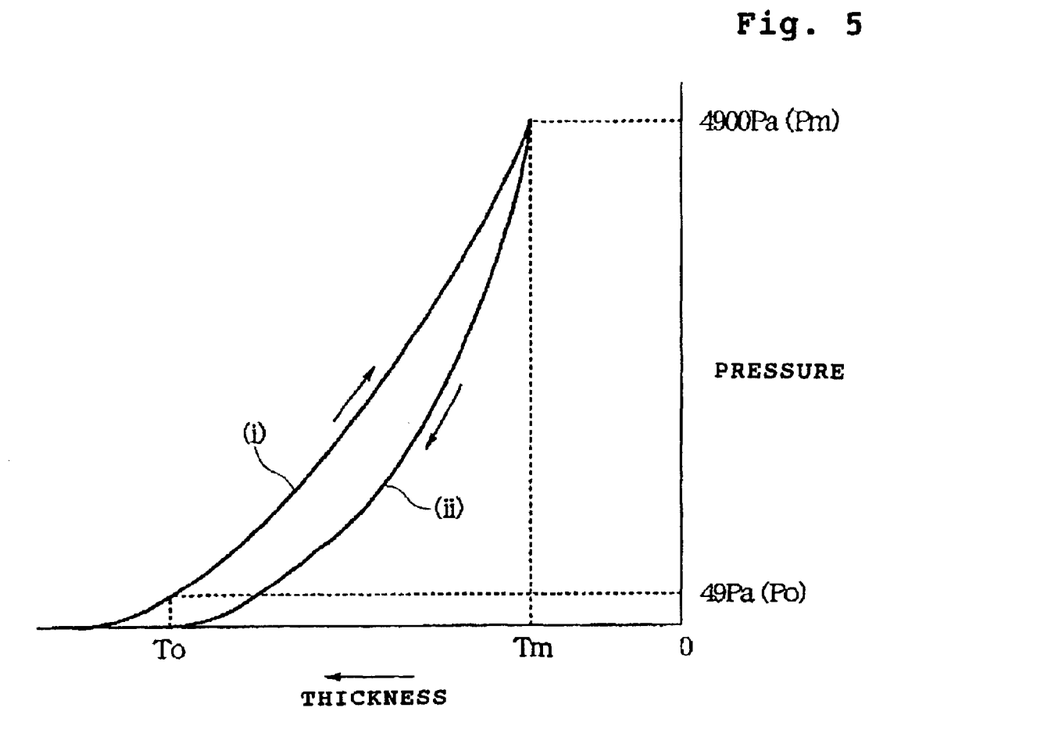
FIG. 5 is a diagram explaining a compression property value.

The outline of the compression property value (LC value) is as follows. In the diagram of FIG. 5, the applied pressure is plotted in ordinate, and the thickness of test sample is plotted in abscissa. The initial thickness T0 refers to the thickness (T1 or T2) of the pressed region of the test sample when the initial pressure of P0=49 Pa (0.5 g/cm²) is applied thereto with the pressure plate. Then, the compression pressure is increased linearly at a compression rate of 50 mm/second from the initial pressure P0 to the maximum compression pressure of Pm=4,900 Pa (50 g/cm²). The thickness Tm refers to the thickness of the pressed region of the test sample when the maximum compression pressure Pm is applied thereto.

The compression energy WC per 1 cm² of the test sample is expressed by a value of the definite integral along the curve (i) of FIG. 5 between Tm and T0, i.e., WC=∫P·dT (P indicates pressure; T indicates thickness). Then, the compression property value (LC value) is obtained according to LC=2WC/{(T0−Tm)Pm} (dimensionless).

In the absorbing sheet 1, the cushion layer 4 has a compression property value (LC value) smaller than that of the topsheet 5. Preferably, The LC value of the cushion layer 4 is 0.1 to 0.5 times the LC value of the topsheet 5.

The cushion layer 4 is not limited to the through-air bonded nonwoven fabric, but may be formed from any suitable nonwoven fabrics such as spunlaced nonwoven fabric as long as the thickness T2 and the compression property value (LC value) thereof can be set within the foregoing ranges.

The through-air bonded nonwoven fabric comprises thermoplastic synthetic fibers, such as monocomponent synthetic fibers of polyethylene (PE), polypropylene (PP) or polyethylene terephthalate (PET), bicomponent synthetic fibers of combinations thereof, or nylon (Ny) fibers.

In case where the cushion layer 4 mainly comprises hydrophobic synthetic fibers, the topsheet 5 mainly serves the function of absorbing a liquid, and the cushion layer 4 substantially does not function to retain a liquid, as in the case (2). However, it is also possible that the cushion layer 4 contains at most 20% by weight of hydrophilic fibers such as cotton or rayon in addition to the synthetic fibers, thereby enabling the cushion layer 4 to absorb moisture or allowing a small amount of liquid to enter the cushion layer 4. In this case, too, the topsheet 5 dominantly functions as a layer for substantially absorbing a liquid, and the cushion layer 4 substantially does not function as a layer for retaining a liquid.

On the other hand, in case where the cushion layer 4 is formed from a through-air bonded or spunlaced nonwoven fabric comprising synthetic fibers treated to be hydrophilic, a through-air bonded or spunlaced nonwoven fabric containing hydrophilic fibers such as rayon or pulp in addition to the synthetic fibers treated to be hydrophilic, or a spunlaced nonwoven fabric only of the hydrophilic fibers, the cushion layer 4 substantially functions as an absorbent layer having the function of absorbing and retaining a liquid, as in the case (1).

In the main body 2 of the absorbing sheet 1, as set forth above, the initial thickness T1 of the topsheet 5 is 0.5 to 5 mm, and the initial thickness T2 of the cushion layer 4 is preferably 1 to 5 times the thickness T1. However, it is also preferred that the total thickness (T1+T2) of the topsheet 5 and the cushion layer 4 ranges between 1 and 10 mm. In this case, T1 is 0.5 mm and T2 is 0.5 mm at the minimum (i.e., when the total thickness is 1 mm); T1 is 5 mm and T2 is 5 mm at the maximum (i.e., when the total thickness is 10 mm). More preferably, the thickness T1 is 0.5 to 3 mm, the thickness T2 is 1 to 5 times the thickness T1, and the total thickness (T1 +T2) ranges between 1 and 6 mm. In this case, T1 is 0.5 mm and T2 is 0.5 mm at the minimum; T1 is 3 mm and T2 is 3 mm at the maximum.

The topsheet 5 and the cushion layer 4 are bonded to each other with a hot-melt type adhesive or the like. FIG. 2 shows vacant spaces 5a left between the upper surface of the cushion layer 4 and the topsheet 5 thus bonded. However, the upper surface of the cushion layer 4 may be undulated to eliminate such vacant spaces 5a.

On the other hand, the pressure sensitive adhesive layer 6 is of the hot-melt type and adheres to the undergarment at a peelable adhesive strength. The release sheet 7 is formed by coating the surface of paper with a release resin layer such as silicone.

Upon wearing, after the release sheet 7 is peeled off, the absorbing sheet 1 is fixed on the inner side of the crotch portion of the undergarment through the pressure sensitive adhesive layer 6. Then, the absorbing sheet 1 is worn by a wearer together with the undergarment so that the topsheet 5 comes into contact with the wearer's skin. Here, since the topsheet 5 has the ridge portions 21 and the groove portions 22 arranged at a small pitch, the topsheet 5 can provide a soft contact feeling to the wearer's skin. In addition, since the cushion layer 4 is disposed beneath the topsheet 5, the cushion layer 4 can relieve the contact pressure to the wearer's skin, together with the topsheet 5, thereby improving the wearing feel.

Since the cushion layer 4 is positioned beneath the topsheet 5 and the thickness T2 of the cushion layer 4 is equal to or larger than the thickness T1 of the topsheet 5 and the compression property value (LC value) of the cushion layer 4 is smaller than that of the topsheet 5, even if a pressure acts on the topsheet 5 in the manufacturing process, such pressure is relieved by contraction of the cushion layer 4, thereby preventing the difference in level between the ridge portions 21 and the groove portions 22 of the topsheet 5 from being removed or reduced, so that the shape of the ridge portions 21 and the groove portions 22 can be maintained as it is.

On the other hand, the absorbing sheet is generally folded on two fold lines and the absorbing sheet thus folded is wrapped in a packaging material for sale. Even if a pressure acts in such a folded state, the difference in level between the ridge portions 21 and the groove portions 22 of the topsheet 5 is not easily removed or reduced, as set forth above. Accordingly, when unwrapped, the fine ridge and groove portions 21 and 22 alternating with each other appear on the topsheet 5 to provide a soft appearance.

Figure 3:
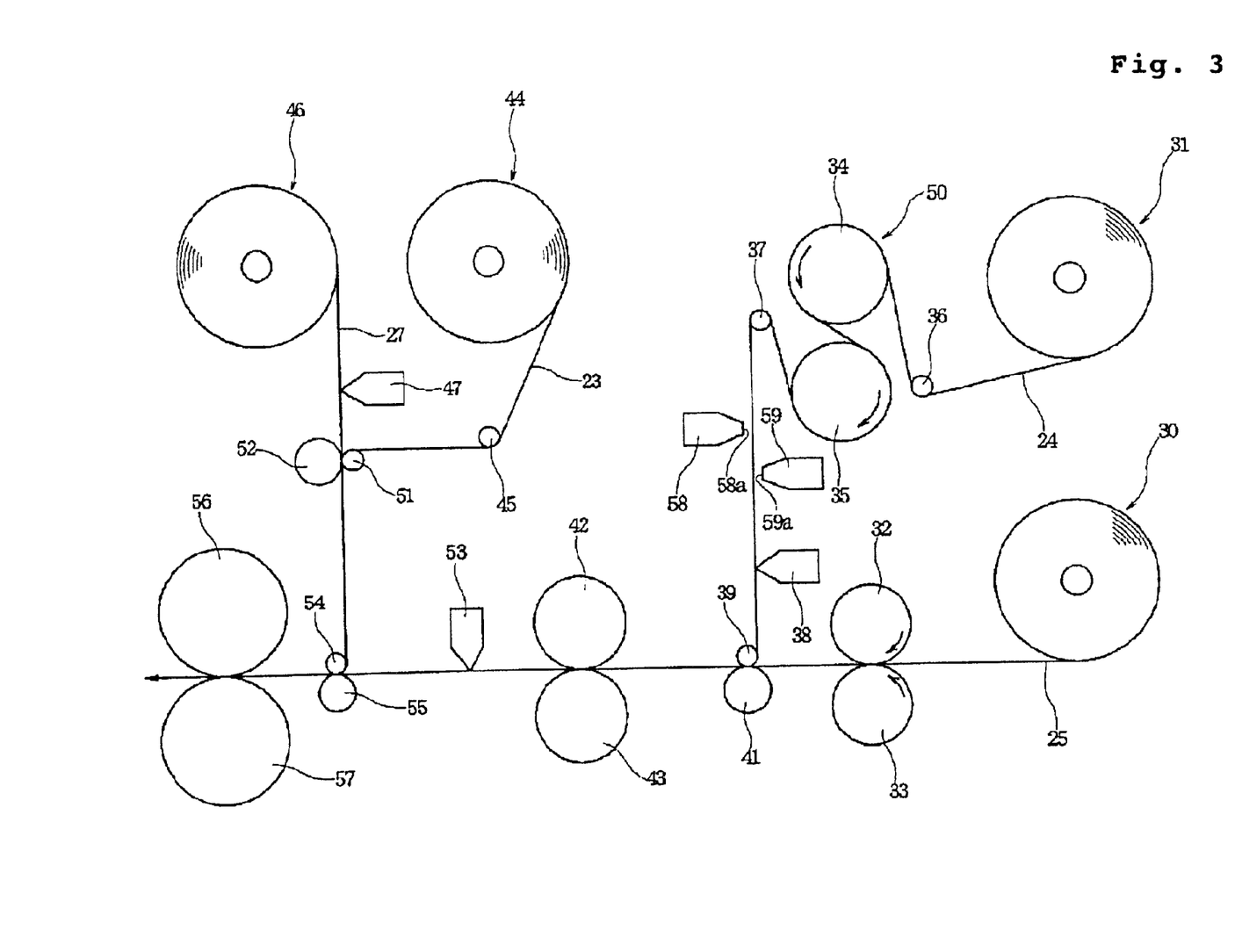
FIG. 3 is an illustration showing one example of a method of manufacturing the absorbent article of FIG. 1.

FIG. 3 shows one example of a method of manufacturing the absorbing sheet 1.

A material roll 30 is formed by winding a nonwoven fabric 25, such as hydrophilic spunlaced nonwoven fabric, for forming the topsheet 5. The nonwoven fabric 25 is fed to a nip between forming rolls 32 and 33. One of the forming rolls 32 and 33 is provided on its surface with protrusions and recesses alternating with each other in the axial direction of the roll and extending parallel with one another in the circumferential direction of the roll. The other roll is provided on its surface with recesses and protrusions adapted to mate with the foregoing protrusions and recesses.

Under a condition where the forming rolls 32 and 33 are heated to about 120° C., the nonwoven fabric 25 is pressed between the forming rolls 32 and 33 while being let out. Thus, ridge portions and groove portions similar to those indicated at 21 and 22 in FIG. 2 are formed in the nonwoven fabric.

A material roll 31 is formed by winding a nonwoven fabric 24, such as the through-air bonded nonwoven fabric, for forming the cushion layer 4. In the material roll 31, the nonwoven fabric 24 is wound with its thickness being reduced.

The nonwoven fabric 24 is fed over a roll 36 to a heating unit 50. The heating unit 50 is provided with heat rolls 34 and 35, the surfaces of which are heated. The nonwoven fabric 24 is wound about these heat rolls 34 and 35 to be heated.

The heat rolls 34 and 35 are spaced apart from each other and their surfaces are smooth. Therefore, the nonwoven fabric 24 is wound and advanced about the respective heat rolls 34 and 35 without being pressed between the heat rolls 34 and 35. At this time, one face of the nonwoven fabric 24 is brought into contact with the surface of the heat roll 34 and heated; the other face of the nonwoven fabric 24 is brought into contact with the surface of the heat roll 35 and heated, so that the nonwoven fabric 24 is heated from both faces with the heat rolls 34 and 35.

In case where the nonwoven fabric 24 is a through-air bonded nonwoven fabric mainly comprising thermoplastic fibers, when heated with the surfaces of the heat rolls 34 and 35, the bulkiness (thickness) of the nonwoven fabric 24 is increased by 1.5 to 8 times to approach the original bulkiness (bulkiness before winding), and the density thereof is decreased to at most $\frac{1}{3}$ to approach the original density (density before winding). In other words, the bulkiness and density of the nonwoven fabric 24 are restored. For example, when the nonwoven fabric 24 is wound into the material roll 31 (i.e., before the restoration of the bulkiness), the thickness measured with the Automatic Compression Tester is 0.5 mm; after the nonwoven fabric 24 passes through the heat rolls 34 and 35 (i.e., after the restoration of the bulkiness), the thickness measured in the same manner is increased to 0.75 to 4 mm.

The surface temperature of the heat rolls 34 and 35 is preferably set equal to or higher than the lowest one of the softening temperatures of the materials forming the through-air bonded nonwoven fabric. In this case, it is more preferred that they are heated up to a temperature equal to or higher than the highest one of the softening temperatures of the materials. For example, in case where the nonwoven fabric 24 is a through-air bonded nonwoven fabric comprising PE fibers, the surface temperature of the heat rolls 34 and 35 is preferably set at about 115° C.

Here, it is not necessarily the only one way to heat the nonwoven fabric 24 with the two heat rolls 34 and 35. For example, the nonwoven fabric 24 may be heated with only one of the heat rolls 34 and 35. In this case, only one face of the nonwoven fabric 24 will be heated. However, since the restoring effect of the bulkiness increases as the heating time of the nonwoven fabric 24 becomes longer, it is preferred to provide two or more heat rolls.

In an alternative to the foregoing construction, it is also possible to provide another heat roll in addition to the heat rolls 34 and 35 so as to heat the nonwoven fabric 24 with three or more heat rolls. By increasing the number of the heat rolls, the heating time of the nonwoven fabric 24 can be made longer to increase the restoring effect of the bulkiness of the nonwoven fabric 24.

After the restoration of the thickness, the nonwoven fabric 24 is fed over a roll 37 to cooling devices 58 and 59. These cooling devices 58 and 59 are paired to confront both faces of the nonwoven fabric 24. The cooling devices 58 and 59 are constructed to blow air from nozzles 58a and 59a, so that the nonwoven fabric 24 is rapidly cooled with the air blown in both faces thereof.

Since the fibers constituting the nonwoven fabric 24 are solidified in a short period of time by cooling the nonwoven fabric 24 after the restoration of the bulkiness with heating, the nonwoven fabric 24 can be immediately set at the bulkiness restored state. Therefore, even when a tensile force is immediately applied to the nonwoven fabric 24 in the subsequent transporting process, the nonwoven fabric 24 can certainly maintain the restored bulkiness.

Especially in case where the nonwoven fabric 24 is a through-air bonded nonwoven fabric comprising thermoplastic fibers, the materials forming the nonwoven fabric can be cooled to a temperature lower than the softening temperatures thereof. Therefore, even if such tensile force is applied, the nonwoven fabric 24 is prevented from extending and decreasing in bulkiness.

In this embodiment, since the nonwoven fabric 24 is cooled by applying air with the cooling devices 58 and 59, a large pressure, which might otherwise reduce the bulkiness, hardly acts on the nonwoven fabric 24 in the cooling process.

After cooling with the cooling devices 58 and 59, the nonwoven fabric 24 is coated with a hot-melt type adhesive, which is applied in a wavy or spiral pattern by nozzles 38 provided downstream from the cooling devices 58 and 59. Then, the nonwoven fabric 25 and the nonwoven fabric 24 are stacked and fed to a nip between rolls 39 and 41, thereby bonding the nonwoven fabric 25 and the nonwoven fabric 24 to each other through the hot-melt type adhesive.

The nonwoven fabrics 24 and 25 thus bonded are fed to a nip between rolls 42 and 43. One of the rolls 42 and 43 is provided on its surface with protrusions patterned to form the seal portion 16 shown in FIG. 2. The other roll has a smooth surface. The rolls 42 and 43 are heated to about 125° C., so that the bonded nonwoven fabrics 24 and 25 are heated under pressure between the rolls 42 and 43 to form the seal portion 16.

In case where the nonwoven fabric 24 is a through-air bonded nonwoven fabric comprising thermoplastic fibers, the thermoplastic fibers forming the through-air bonded nonwoven fabric are melted in the seal portion 16, thereby fusion-bonding the nonwoven fabrics 24 and 25 to each other.

A material roll 44 is formed by winding a moisture impermeable film 23 for forming the backsheet 3. This film 23 is unwound through a roll 45. A material roll 46 is formed by winding a release paper 27 coated with release resin layer for forming the release sheet 7. The pressure sensitive adhesive layer 6 is formed by applying a hot-melt type adhesive from nozzles 47 onto the release paper 27 unwound from the material roll 46. The release paper 27 and the film 23 are pressed between rolls 51 and 52 so that they can be adhered to each other through the pressure sensitive adhesive layer 6.

A hot-melt type adhesive is applied from nozzles 53 onto the surface of the nonwoven fabric 24 of the composite of the nonwoven fabrics 25 and 24 having the seal portion 16 formed with the rolls 42 and 43. Between rolls 54 and 55, thereafter, the nonwoven fabric 24 is bonded to the film 23 under pressure to form a laminate of the nonwoven fabric 25, the nonwoven fabric 24, the film 23 and the release paper 27.

Then, the laminated is fed and trimmed between cutter rolls 56 and 57 to thereby cut the absorbing sheet 1 having the shape of FIG. 1.

Figure 4:
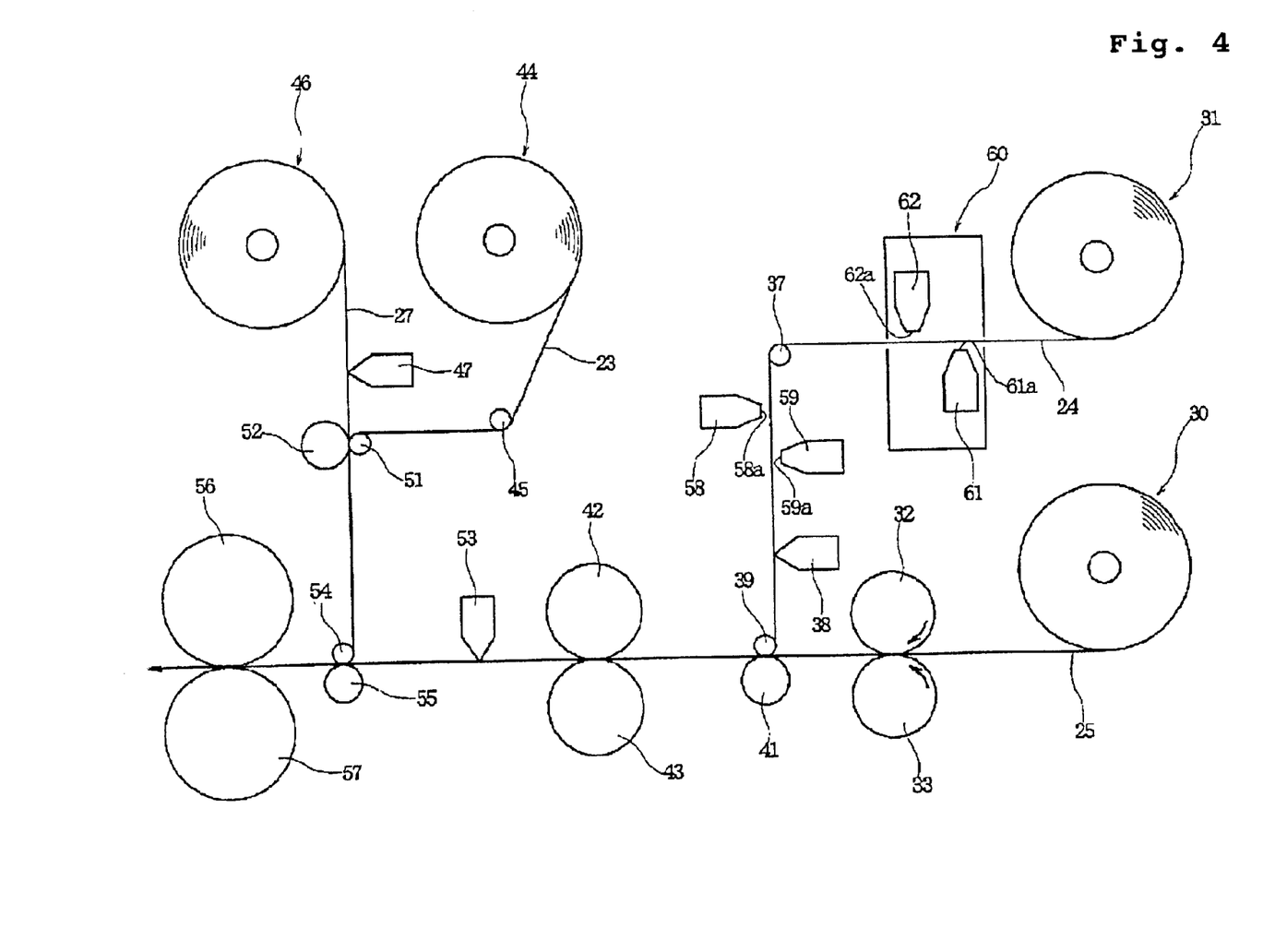
FIG. 4 is another illustration showing one example of a method of manufacturing the absorbent article of FIG. 1.

FIG. 4 shows another example of a method of manufacturing the absorbing sheet 1. In the manufacturing method shown in FIG. 4, the detailed description of the portions having the same constructions as those in the manufacturing method shown in FIG. 3 will be omitted by designating them by the common reference numerals.

In the manufacturing method shown in FIG. 4, the nonwoven fabric 24 wound into the material roll 31 is unwound and fed to a heat chamber 60. In the heat chamber 60, there are provided two heating devices 61 and 62, which are paired to confront both faces of the nonwoven fabric 24. From discharge openings 61a and 62b of the heating devices 61 and 62, heated air is discharged and applied to the nonwoven fabric. For example, in case where the nonwoven fabric 24 is the through-air bonded nonwoven fabric, the nonwoven fabric is heated to about 115° C. with the heated air.

In the embodiment shown in FIG. 4, the nonwoven fabric 24 can be efficiently heated by applying heated air to the nonwoven fabric 24 within the heat chamber 60. In addition, since the paired heating devices 61 and 62 apply heated air to both faces of the nonwoven fabric 24, the entire nonwoven fabric 24 can be easily heated. Moreover, since the nonwoven fabric 24 in the heat chamber 60 is not pressed against the roll surface or the like, the restoration of the bulkiness can be effectively performed. Here, it is also possible to heat only one face of the nonwoven fabric 24 with the heating device.

Figure 6:
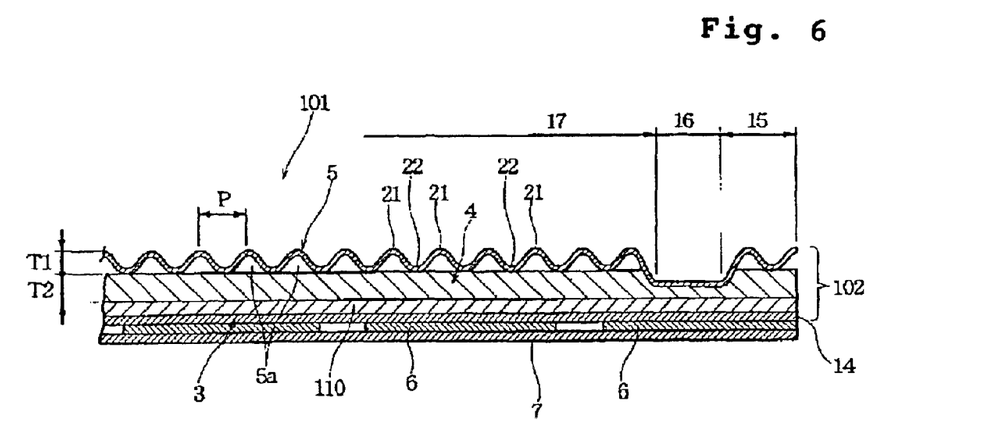
FIG. 6 is a sectional view of a portion of a vaginal discharge absorbing sheet as an absorbent article according to a second embodiment of the present invention.

FIG. 6 is a sectional view of a portion of a vaginal discharge absorbing sheet (hereinafter referred to as "absorbing sheet 101") according to a second embodiment of the present invention, which corresponds to FIG. 2.

In the absorbing sheet 101 shown in FIG. 6, the detailed description of the portions having the same constructions as those of the absorbing sheet 1 shown in FIG. 2 will be omitted by designating them by the common reference numerals.

The absorbing sheet 101 of FIG. 6 has a main body 102, in which an absorbent layer 110 having the function of absorbing and retaining a liquid is disposed between the backsheet 3 and the cushion layer 4.

The absorbent layer 110 is trimmed in the same shape and size as the backsheet 3, the cushion layer 4, the topsheet 5 and the release sheet 7.

For the absorbent layer 110, preferably used is an air laid nonwoven fabric, which is formed such that pulp mixed with heat-fusible synthetic fibers as binder is suspended in air, collected and accumulated on a screen, and then heated to bond the pulp to each other through the binder into a sheet form. For example, the air laid nonwoven fabric is formed by mixing 87% of pulp with 13% of sheath/core fibers of PP/PE (1.7 dtex, fiber length 13 mm). In an alternative, an air laid nonwoven fabric formed by mixing pulp with powdery heat-fusible resin as binder, or formed only of pulp without any binder, may also be used. In another alternative, an air laid nonwoven fabric formed by mixing pulp (containing or not containing the binder) with superabsorbent polymer or regenerated cellulose fibers may also be used. Here, as the pulp, preferably used is wood pulp.

For the absorbent layer 110, the air laid nonwoven fabric wound into the form of material roll is unwound from the material roll and heated with a heat roll or by applying heated air to restore the bulkiness (thickness) within a range from 5 to 20%. The heating temperature is preferably set to at least 100° C.

The air laid nonwoven fabric preferably has a basis weight in a range between 40 and 400 $g/m^2$ and a fiber density of 0.05 to 0.2 $g/cm^3$ after the restoration of the bulkiness.

With the main body 102 thus constructed to include the absorbent layer 110, when menstruation occurs during wear of the absorbing sheet 101, for example, excess menstrual blood which cannot be retained by the topsheet 5 and the cushion layer 4 is absorbed and retained by the absorbent layer 110, thereby preventing the undergarment from being soiled until a sanitary napkin or the like is worn.

In addition to the foregoing effect, in case where the main body 102 is constructed to have four layers including the absorbent layer 110, if the absorbent layer 110 is formed from a material of which bulkiness is restored by heating as well as the cushion layer 4, it becomes easier to prevent the ridge portions 21 and the groove portions 22 formed in the topsheet from being crushed.

Figure 7:
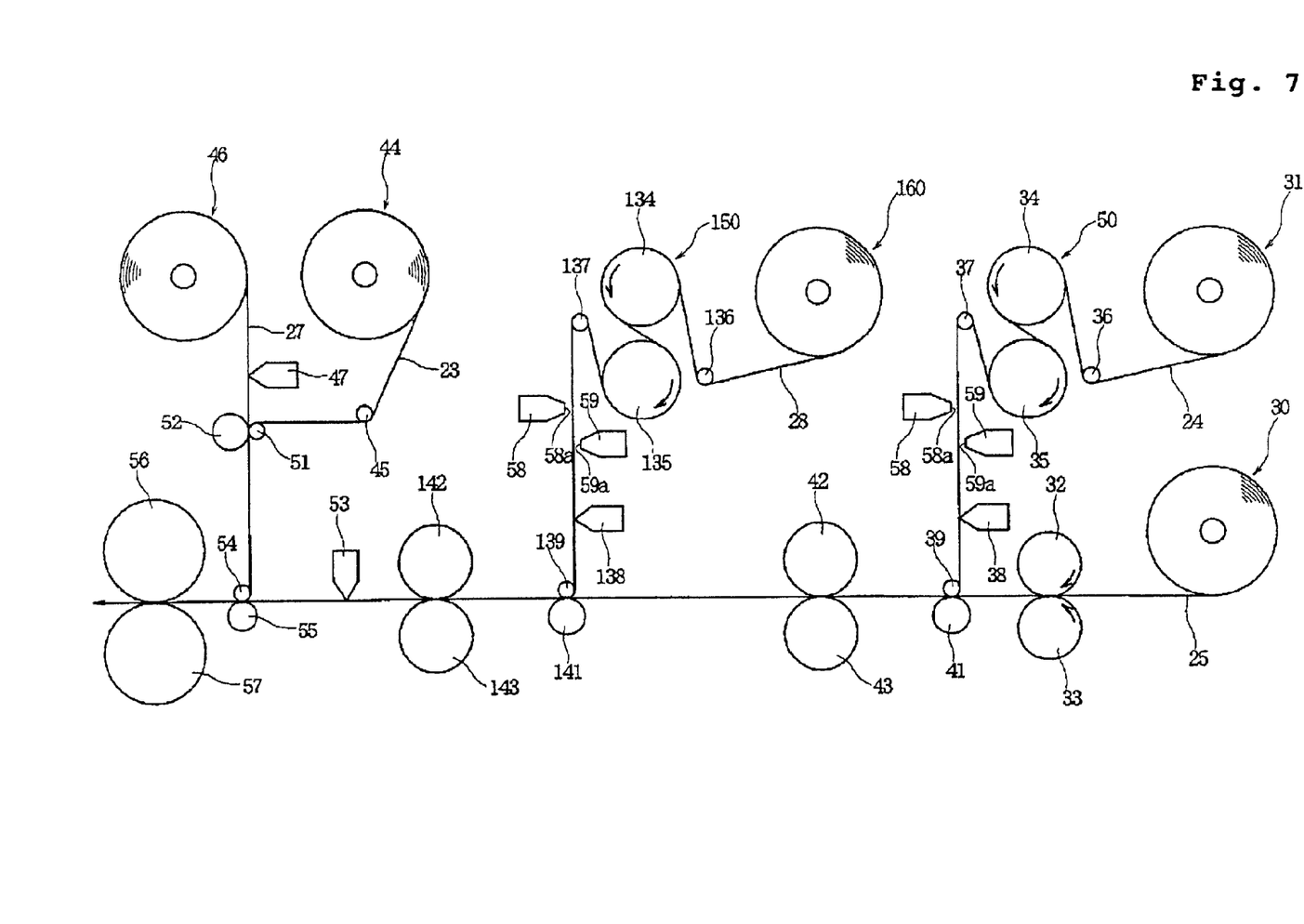
FIG. 7 is an illustration showing one example of a method of manufacturing the absorbent article of FIG. 6.

FIG. 7 shows one example of a method of manufacturing the absorbing sheet 101. In the manufacturing method shown in FIG. 7, the detailed description of the portions having the same constructions as those in the manufacturing method shown in FIG. 3 will be omitted by designating them by the common reference numerals.

A material roll 160 is formed by winding a nonwoven fabric 28, such as air laid nonwoven fabric comprising pulp, for forming the absorbent layer 110. The nonwoven fabric 28 is wound in a condition where the thickness is reduced.

The nonwoven fabric 28 is fed over a roll 136 to a heating unit 150, in which the nonwoven fabric is heated while being wound about heat rolls 134 and 135 whose surfaces are heated.

In the heating unit 150, too, the heat rolls 134 and 135 are spaced apart from each other and their surfaces are smooth, as in the heating unit 50. Therefore, the nonwoven fabric 28 is wound and advanced about the respective heat rolls 134 and 135 to be heated from both faces, without being pressed between the heat rolls 134 and 135.

The nonwoven fabric 28 is heated with the surfaces of the heat rolls 134 and 135 to restore its bulkiness (thickness). For example, in case of an air laid nonwoven fabric comprising pulp mixed with heat-fusible synthetic fibers, the bulkiness is increased by 1.2 to 1.6 times to approach the original bulkiness.

For example, when the nonwoven fabric 28, which is the air laid nonwoven fabric comprising pulp mixed with heat-fusible synthetic fibers, is wound into the material roll 160 (i.e., before the restoration of the bulkiness), the thickness measured with the Automatic Compression Tester is 1.6 mm; after the nonwoven fabric 28 passes through the heat rolls 134 and 135 (i.e., after the restoration of the bulkiness), the thickness measured in the same manner is increased to 1.9 to 2.4 mm.

Moreover, since the nonwoven fabric 28 is the air laid nonwoven fabric comprising pulp, the surface temperature of the heat rolls 134 and 135 is preferably at least 100° C. By applying heat to the air laid nonwoven fabric with the respective heat rolls at such temperature, the bulkiness of the air laid nonwoven fabric can be much increased.

In the manufacturing method of the absorbing sheet 101 shown in FIG. 7, too, it is possible to heat the nonwoven fabric with only one of the heat rolls 134 and 135. In alternative to the foregoing construction, it is also possible to provide another heat roll in addition to the heat rolls 134 and 135 so as to heat the nonwoven fabric 28 with three or more heat rolls.

After the restoration of the thickness, the nonwoven fabric 28 is then fed over a roll 137 to the cooling devices 58 and 59 for rapid cooling, as in the manufacturing method of the absorbing sheet 1 shown in FIG. 3. In case of the nonwoven fabric 28, too, the bulkiness restored state can be immediately set by rapid cooling, and a large pressure, which might otherwise reduce the bulkiness, hardly acts on the nonwoven fabric 28 in the course of cooling.

After cooling with the cooling devices 58 and 59, the nonwoven fabric 28 is coated with a hot-melt type adhesive, which is applied in a wavy or spiral pattern by nozzles 138 provided downstream from the cooling devices 58 and 59. Then, the nonwoven fabric 28 is fed to a nip between rolls 139 and 141 and bonded to the composite of the nonwoven fabrics 25 and 24 under pressure to thereby form a three-layer composite.

The three-layer composite is fed to a nip between rolls 142 and 143, and then a hot-melt type adhesive is applied from the nozzles 53 onto the surface of the nonwoven fabric 28.

Between the rolls 54 and 55, thereafter, the three-layer composite is bonded under pressure to the film 23, which has the release paper 27 adhered thereon, to form a laminate of the nonwoven fabric 25, the nonwoven fabric 24, the nonwoven fabric 28, the film 23 and the release paper 27.

Then, the laminated is fed and trimmed between the cutter rolls 56 and 57 for cutting.

EXAMPLES

Examples according to the present invention will be described hereinbelow, but the present invention should not be construed as limited thereto.

First, absorbing sheets were prepared as in following Example 1, Example 2 and Comparative Example.

(1) Example 1

Topsheet

A fiber suspension formed by suspending a mixture of 55% by weight of rayon, 30% by weight of PET fibers and 15% by weight of PP fibers in water, was fed onto a net wire to form a wet fiber web, and then, the fibers were entangled about each other with jets of water to produce a wet laid spunlaced nonwoven fabric having a basis weight of 38 g/m$^2$. Thereafter, ridge portions and groove portions were formed in the nonwoven fabric at a pitch P=2 mm with forming rolls. When measured using the Automatic Compression Tester "KES FB-3A" from Kato Tech, the thickness was 1 mm at a pressure of 49 Pa, and the compression property value (LC value) was 0.83.

Cushion Layer

98% by weight of sheath/core structure bicomponent thermoplastic synthetic fibers (2.2 dtex, fiber length 44 mm), of which the core was made of PET containing 1.0% by weight of titanium oxide and the sheath was made of PE, and 2% by weight of cotton fibers having a fiber length of 20 to 30 mm were formed into a through-air bonded nonwoven fabric having a basis weight of 25 g/m$^2$. This through-air bonded nonwoven fabric was heated with heat rolls at a temperature of 115° C. to restore its thickness. The through-air bonded nonwoven fabric after the restoration of the thickness had a thickness of 1.8 mm at a pressure of 49 Pa and a compression property value (LC value) of 0.372, as measured using the Automatic Compression Tester "KES FB-3A" from Kato Tech.

Backsheet

Used was a polyethylene film having a basis weight of 22.5 g/m$^2$.

(2) Example 2

Topsheet and Backsheet

Sheets identical to those in Example 1 were used.

Cushion Layer

Eccentric sheath/core structure bicomponent thermoplastic synthetic fibers (4.4 dtex, fiber length 50 mm), of which the core was made of PP and the sheath was made of PE, were formed into a through-air bonded nonwoven fabric having a basis weight of 20 g/m$^2$. This through-air bonded nonwoven fabric was heated with heat rolls at a temperature of 115° C. to restore its thickness. The through-air bonded nonwoven fabric after the restoration of the thickness had a thickness of 3.0 mm at a pressure of 49 Pa and a compression property value (LC value) of 0.312, as measured using the Automatic Compression Tester "KES FB-3A" from Kato Tech.

(3) Comparative Example

Topsheet and Backsheet

Sheets identical to those in Example 1 were used.

Cushion Layer

Sheath/core structure bicomponent thermoplastic synthetic fibers (2.2 dtex, fiber length 51 mm), of which the core was made of PET and the sheath was made of PE, were treated with heated air into a through-air bonded nonwoven fabric having a basis weight of 30 g/m$^2$. The thickness restoring process using the heat rolls was not performed. This through-air bonded nonwoven fabric had a thickness of 0.8 mm at a pressure of 49 Pa and a compression property value (LC value) of 0.652, as measured using the Automatic Compression Tester "KES FB-3A" from Kato Tech.

(4) Evaluation for Compression

The individual absorbing sheets of Example 1, Example 2 and Comparative Example were cut to a size of 25×25 mm, and then pressed with a roller along the extending direction of the ridge portions and the groove portions. This roller had a length of 45 mm in its axial direction and a weight of 2 kg. The pressing was conducted only once with the rotational speed of the roller being set at 50 mm/min.

After the pressing, the respective topsheets of Example 1, Example 2 and Comparative Example were observed and evaluated by ten monitors according to the following criterion.

Evaluation "∘": The surface looks solid and seems to provide a comfortable contact feel to the touch.

Evaluation "Δ": The surface looks solid and seems to provide a little bit improved contact feel to the touch than ever.

Evaluation "X": The surface does not look solid.

(5) Result

After such compression, the thickness of each topsheet was measured under no-load condition. As a result, the thicknesses of Examples 1 and 2 were both 0.9 mm; the thickness of Comparative Example was 0.5 mm.

According to the monitor test, on the other hand, Examples 1 and 2 were both evaluated as "∘" by all the monitors; Comparative Example was evaluated as "X" by all the monitors.

From the above, it is understood that if the thickness of the cushion layer is equal to or larger than that of the topsheet, the difference in level between the ridge portions and the groove portions of the topsheet is not removed or reduced.

As has been described hereinabove, although the absorbent article according to the present invention is thin, the difference in level between the hills and valleys formed in the topsheet is hardly removed or reduced by an external pressure, thereby constantly providing a soft appearance and a comfortable contact feeling.

In the absorbent article manufacturing method according to the present invention, on the other hand, even if the nonwoven fabric is in a compressed state when supplied from the material roll, it is heated to restore the bulkiness, thereby providing a soft feeling to the absorbent article.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A method for manufacturing an absorbent article including: a topsheet formed from a nonwoven fabric; a backsheet; and a cushion layer disposed between the topsheet and the backsheet, the method comprising:

applying heat to the cushion layer unwound from a material roll to restore bulkiness of the cushion layer;

blowing air into the cushion layer for rapid cooling after the application of heat to maintain the restored bulkiness of the cushion layer; and laminating the topsheet, the cushion layer, and the backsheet one onto another.

2. The absorbent article manufacturing method as set forth in claim 1, wherein the cushion layer is formed from a through-air bonded nonwoven fabric comprising thermoplastic fibers.

3. The absorbent article manufacturing method as set forth in claim 1, which further comprises disposing an absorbent layer, which has a function of absorbing and retaining a liquid, between the cushion layer and the backsheet.

4. The absorbent article manufacturing method as set forth in claim 3, which further comprises applying heat to the absorbent layer unwound from a material roll to restore bulkiness of the absorbent layer, before disposing the absorbent layer between the cushion layer and the backsheet.

5. The absorbent article manufacturing method as set forth in claim 4, which further comprises cooling the absorbent layer after applying heat to the absorbent layer.

6. The absorbent article manufacturing method as set forth in claim 3, wherein the absorbent layer is formed from an air-laid nonwoven fabric comprising pulp.

7. The absorbent article manufacturing method as set forth in claim 1, wherein the topsheet is three-dimensionally shaped to have hills and valleys alternating with each other, the hills and the valleys being arranged at a pitch of 0.5 to 5 mm, the three-dimensionally shaped topsheet having a thickness of 0.5 to 5 mm under a condition where a pressure of 49 Pa is applied thereto.

* * * * *